(12) United States Patent
Kato et al.

(10) Patent No.: US 6,371,941 B1
(45) Date of Patent: Apr. 16, 2002

(54) PREFILLED SYRINGE

(75) Inventors: Masahiko Kato, Amagasaki; Jiichi Arai, Nishinomiya; Makoto Kakiuti, Takahagi, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/150,768

(22) Filed: Sep. 10, 1998

(30) Foreign Application Priority Data

Sep. 16, 1997 (JP) .............................. 9-250314

(51) Int. Cl.$^7$ ............................................. A61M 5/315
(52) U.S. Cl. ...................... 604/220; 604/225; 604/229
(58) Field of Search ................................ 604/214, 218, 604/220, 225, 227, 228, 229, 231, 235, 221

(56) References Cited

U.S. PATENT DOCUMENTS

| | | | |
|---|---|---|---|
| 2,869,541 A | | 1/1959 | Helmer et al. |
| 4,153,056 A | * | 5/1979 | Silver et al. ................. 604/211 |
| 4,367,738 A | * | 1/1983 | Legendre et al. ............ 604/110 |
| 4,386,606 A | * | 6/1983 | Tretinyak et al. ........... 604/220 |
| 4,711,637 A | * | 12/1987 | Leigh et al. ................. 604/220 |
| 5,181,909 A | * | 1/1993 | McFarlane ................... 604/220 |
| 5,263,934 A | * | 11/1993 | Haak .......................... 604/220 |
| 5,615,772 A | * | 4/1997 | Nagannuma ................. 604/220 |

FOREIGN PATENT DOCUMENTS

| | | |
|---|---|---|
| DE | 35 32 622 | 3/1987 |
| EP | 0 550 767 | 7/1993 |
| EP | 0 793 973 | 9/1997 |
| FR | 2 627 087 | 8/1989 |
| GB | 1 550 308 | 8/1979 |
| JP | 7-7650 | 2/1995 |
| JP | 8-229122 | * 9/1996 |

* cited by examiner

Primary Examiner—Anhtuan T. Nguyen
Assistant Examiner—Michael M Thompson
(74) Attorney, Agent, or Firm—Wenderoth, Lind & Ponack, L.L.P.

(57) ABSTRACT

A prefilled syringe has a tubular body which has an open front end and an open rear end. A front assembly is mounted on an outer periphery of a front end portion of the tubular body. A finger grip is mounted on an outer periphery of a rear end portion of the tubular body. A front sealing member is provided in the tubular body so as to be disposed forwardly of injection liquid and a rear sealing member is provided in the tubular body so as to be disposed rearwards of the injection liquid. A plunger rod is provided so as to be movable in the tubular body. A temporary stop member temporarily stops the plunger rod through retention of the temporary stop member by the finger grip such that the rear sealing member is temporarily stopped at a predetermined position of the tubular body. A retention canceling member cancels the retention of the temporary stop member by the finger grip without moving the plunger rod.

5 Claims, 16 Drawing Sheets

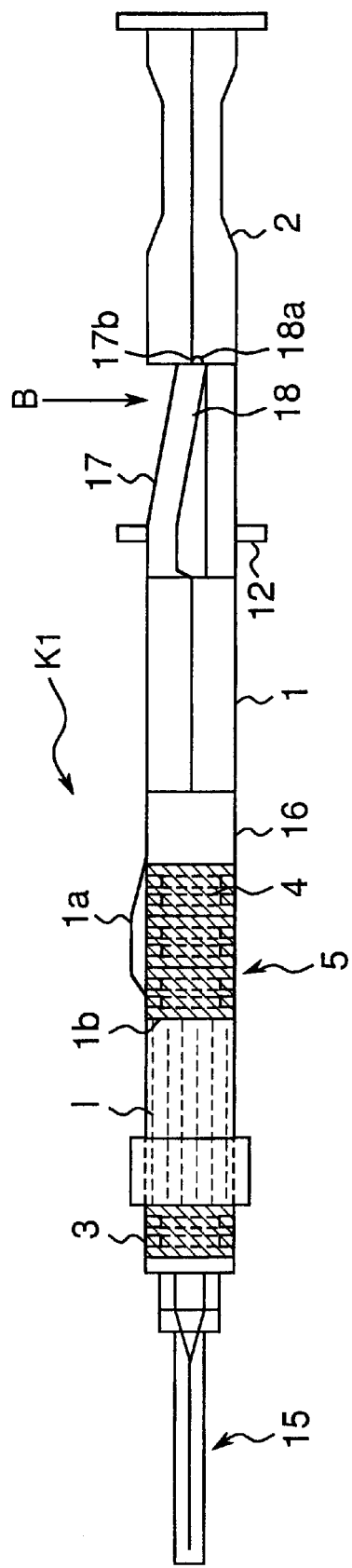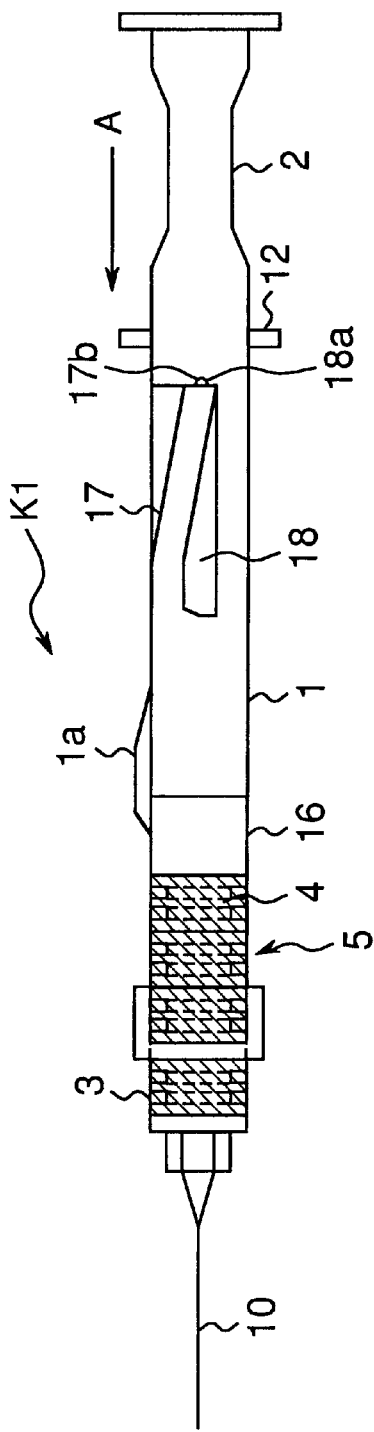

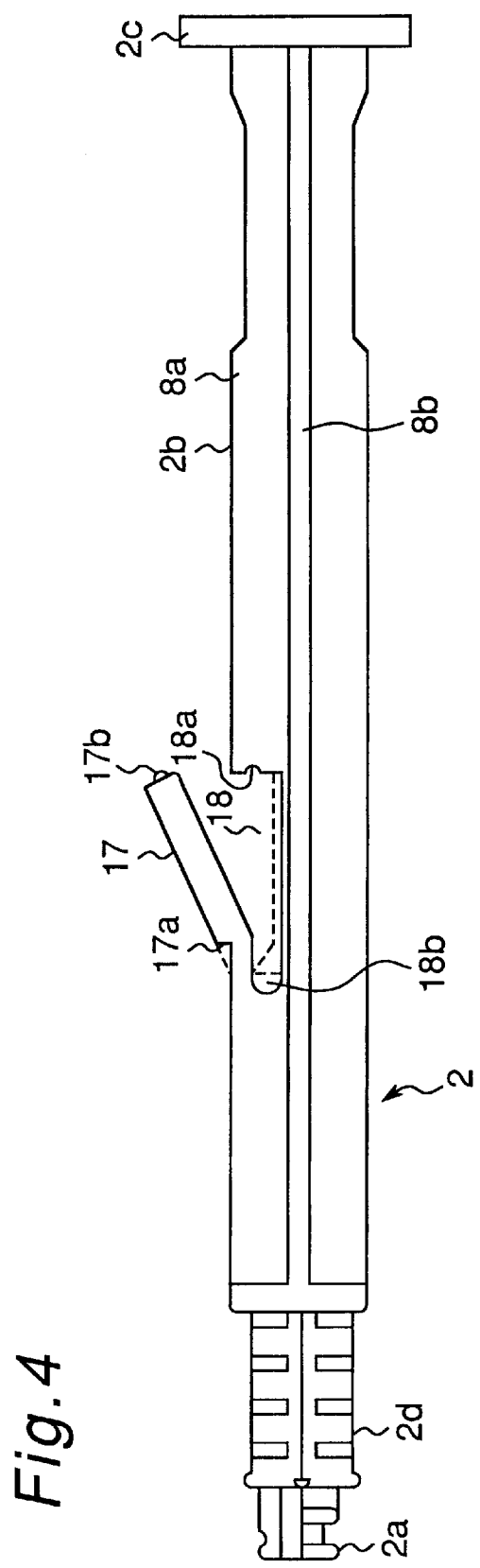

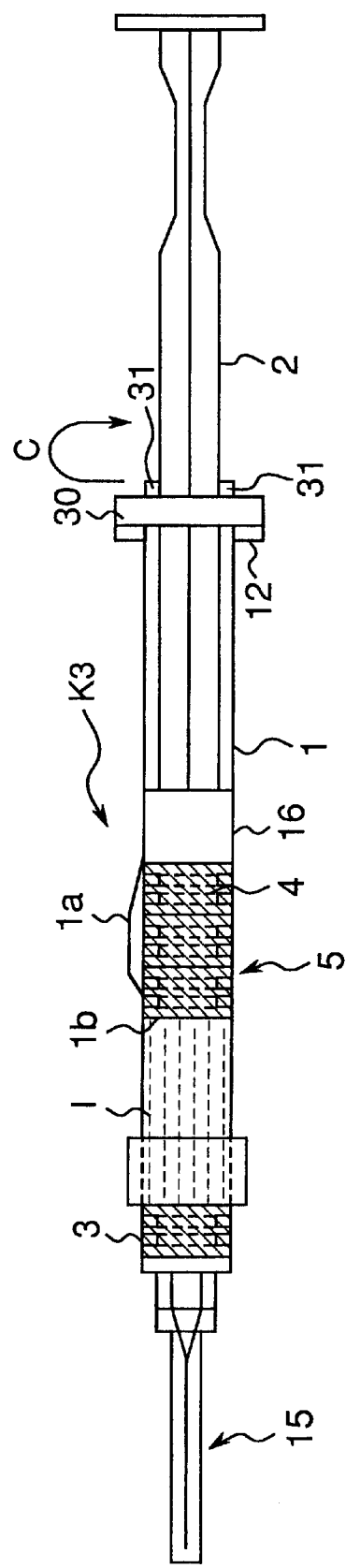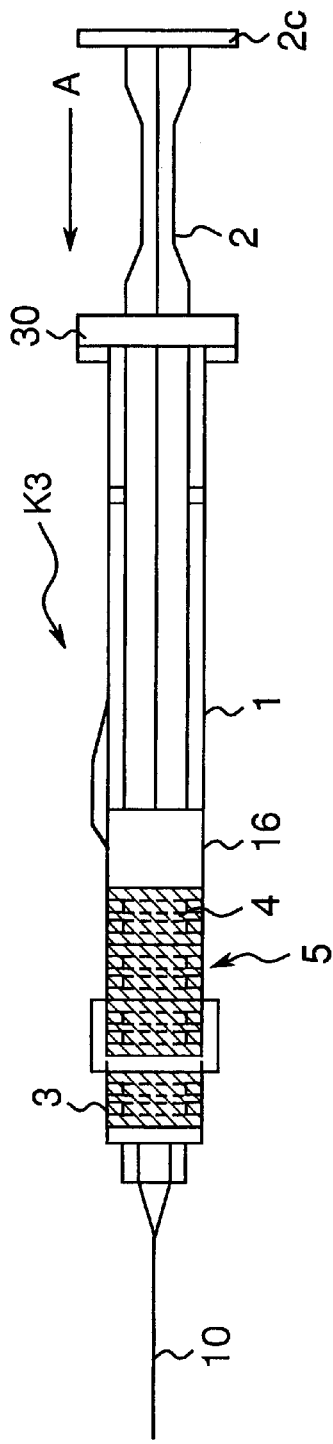
Fig. 12A
Fig. 12B

PREFILLED SYRINGE

BACKGROUND OF THE INVENTION

1. Field of the Invention

The present invention generally relates to single-use syringes in which medicament is filled preliminarily, i.e., so-called prefilled syringes and more particularly, to a prefilled syringe which is provided with a temporary stop means for temporarily stopping a plunger rod at a predetermined position when, in use, the plunger rod is depressed forwardly.

2. Description of the Prior Art

Prior to administration of injection liquid of a two-component type prefilled syringe in which powdery medicament and pharmaceutical liquid are, respectively, contained in front and rear compartments of a tubular body, a plunger rod is stopped temporarily in a state where the pharmaceutical liquid in the rear compartment has fully flowed into the front compartment by depressing the plunger rod. When the powdery medicament is sufficiently dissolved or dispersed in the pharmaceutical liquid by shaking the tubular body in this state, the injection liquid is prepared. Subsequently, by further depressing the plunger rod, the injection liquid is administered.

A prefilled syringe shown in FIGS. 17 and 18 is known from Japanese Utility Model Laid-Open Publication No. 7-7650 (1995). In this known prefilled syringe, a pair of bosses 61 are provided on an inner periphery of a flange 55a of a finger grip 55 mounted on an outer periphery of a rear end portion of a tubular body 52, while a pair of first stopper plates 65 and a pair of second stopper plates 66 are provided between neighboring two of crossed ribs 62 of a plunger rod 60 so as to not only abut on each other through a corresponding one of the ribs 62 but be axially spaced away from each other such that the plunger rod 60 is temporarily stopped by bringing the bosses 61 and the second stopper plates 66 into contact with each other.

However, in this known prefilled syringe, after the first stopper plates 65 have come into contact with the bosses 61 by inserting the bosses 61 through recesses 64 formed on a front end flange 63 of the plunger rod 60, the plunger rod 60 is pulled slightly rearwards and rotated so as to displace the bosses 61 to between the ribs 62 free from the first stopper plates 65. Then, by further depressing the plunger rod 60, the bosses 61 come into contact with the second stopper plates 66. Subsequently, after the bosses 61 and the second stopper plates 66 have been brought out of contact with each other by rotating the plunger rod 60 until the bosses 61 are positioned between the ribs 62 free from the second stopper plates 66, injection liquid is administered by further depressing the plunger rod 60. Therefore, this known prefilled syringe has such drawbacks that its construction is complicated and its operation is troublesome and difficult.

Meanwhile, Japanese Patent Laid-Open Publication No. 8-229122 (1996) discloses a prefilled syringe in which a forwardly obliquely and radially outwardly extending rodlike projection 70 is formed integrally with a plunger rod 75 as shown in FIG. 19. Even if an external force such as an impact force is applied to this prior art prefilled syringe during its storage, a front end of the rodlike projection 70 is brought into contact with a finger grip 73 so as to temporarily stop the plunger rod 75 such that inadvertent displacement of the plunger rod 75 is prevented. Consequently, such a phenomenon is eliminated that medicament filled in the prior art prefilled syringe undesirably linking from an injection needle is eliminated.

In the prior art prefilled syringe of FIG. 19, after the plunger rod 75 has been temporarily stopped, the rodlike projection 70 is inserted into a slot 76 of the plunger rod 75 such that a sharp edge 70a of a front end face of the rodlike projection 70 is brought into engagement with a recess 76a of the slot 76. Then, by depressing the plunger rod 75, injection liquid is administered. However, while the plunger rod 75 is being stopped temporarily, the front end of the rodlike projection 70 is held in contact with the finger grip 73. Thus, when an attempt is made to push the rodlike projection 70 downwardly in this state, the front end of the rodlike projection 70 is pressed against the finger grip 73 further powerfully, so that it is difficult to insert the rodlike projection 70 into the slot 76. As a result, in this prior art prefilled syringe, when the rodlike projection 70 is inserted into the slot 76, the rodlike projection 70 held in contact with the finger grip 73 should be spaced away from the finger grip 73 by retracting the plunger rod 75 and then, the rodlike projection 70 is required to be inserted into the slot 76. Therefore, this prior art prefilled syringe has such a disadvantage in that air is sucked into tubular body 71 from an injection needle upon retraction of the plunger rod 75.

Furthermore, in this prior art prefilled syringe, since the front end of the forwardly obliquely and radially outwardly extending rodlike projection 70 is brought into contact with a rear end face of the finger grip 73, the front end of the rodlike projection 70 is apt to slide upwardly on the rear end face of the finger grip 73, thereby resulting in an inconvenience in that the temporary stop of the plunger rod 75 becomes unstable.

SUMMARY OF THE INVENTION

Accordingly, an essential object of the present invention is to provide, with a view toward eliminating the above described drawbacks of conventional prefilled syringes, a prefilled syringe which is simple in structure and easy in operation, which eliminates a risk that air is sucked into a tubular body from an injection needle and which is provided with a temporary stop means capable of temporarily positively stopping a plunger rod.

In order to accomplish this object of the present invention, a prefilled syringe according to the present invention comprises: a tubular body which has an open front end and an open rear end; a front assembly which is mounted on an outer periphery of a front end portion of the tubular body; a finger grip which is mounted on an outer periphery of a rear end portion of the tubular body; a front sealing member which is provided in the tubular body so as to be disposed forwardly of injection liquid; a rear sealing member which is provided in the tubular body so as to be disposed rearwards of the injection liquid; a plunger rod which is provided so as to be movable in the tubular body; a temporary stop means for temporarily stopping the plunger rod through retention of the temporary stop means by the finger grip such that the rear sealing member is temporarily stopped at a predetermined position of the tubular body; and a retention canceling means for canceling the retention of the temporary stop means by the finger grip without moving the plunger rod.

The temporary stop means may be constituted by a retainer member which is elastically formed integrally with the plunger rod so as to project rearwards obliquely relative to an axis of the plunger rod and radially outwardly from the plunger rod and is retained by the finger grip upon contact of a base portion of the retainer member with a rear end face of the finger grip, while the retention canceling means may include a hollow which is formed on the plunger rod so as to receive the retainer member.

BRIEF DESCRIPTION OF THE DRAWINGS

This object and features of the present invention will become apparent from the following description taken in conjunction with the preferred embodiments thereof with reference to the accompanying drawings in which:

FIGS. 2A and 2B are schematic sectional views showing a third operational position and a fourth operational position of the two-component type prefilled syringe of FIG. 1A, respectively;

FIG. 4 is an enlarged front elevational view of the plunger rod of FIG. 3;

FIGS. 12A and 12B are schematic sectional views showing a third operational position and a fourth operational position of the two-component type prefilled syringe of FIG. 11A, respectively;

Before the description of the present invention proceeds, it is to be noted that like parts are designated by like reference numerals throughout several views of the accompanying drawings.

DETAILED DESCRIPTION OF THE INVENTION

Figure 3:
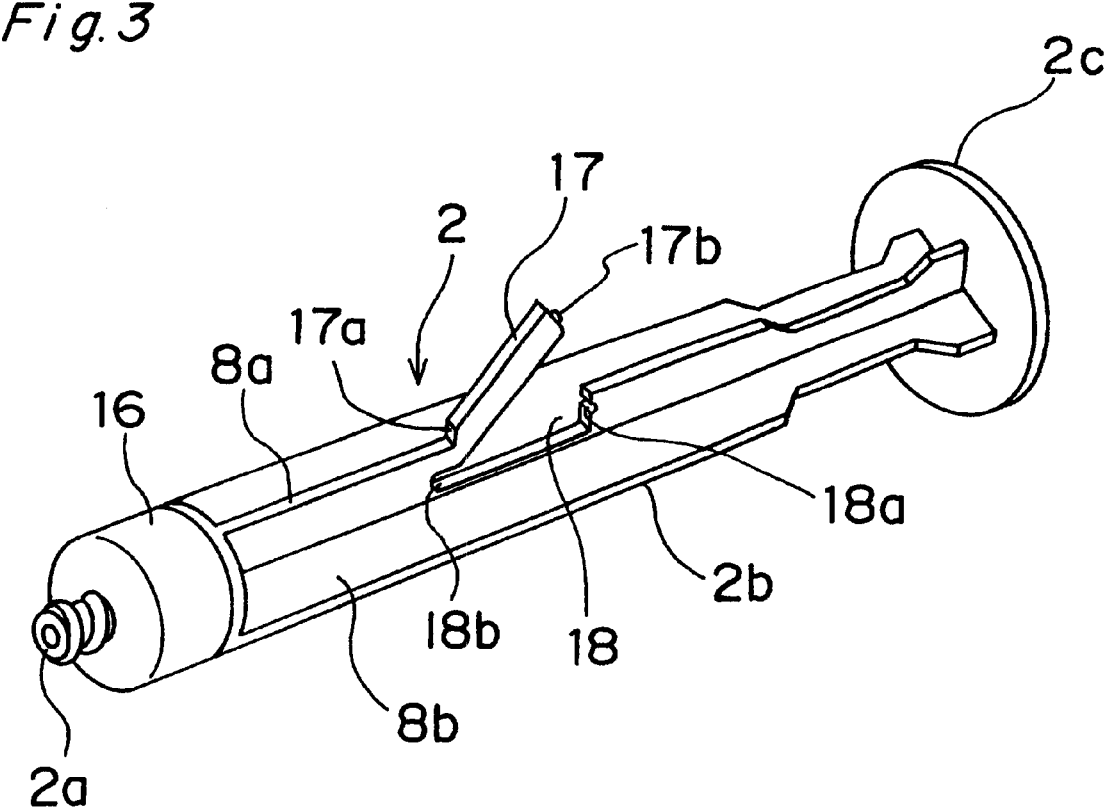
FIG. 3 is a perspective view of a plunger rod of the two-component type prefilled syringe of FIG. 1A.

Referring now to the drawings, FIGS. 1A and 1B and FIGS. 2A and 2B show a first operational position (storage position), a second operational position, a third operational position and a fourth operational position of a two-component type prefilled syringe K1 according to a first embodiment of the present invention, respectively. The two-component type prefilled syringe K1 includes an elongated hollow tubular body 1 having an open front end and an open rear end, a first sealing member 3 mounted in a front end portion of the tubular body 1, a second sealing member 4 mounted in a rear end portion of the tubular body 1, an intermediate sealing member 5 slidably inserted between the first and second sealing members 3 and 4 in the tubular body 1 and a movable plunger rod 2. At the first operational position (storage position) of the two-component type prefilled syringe K1 shown in FIG. 1A, the intermediate sealing member 5 divides interior space of the tubular body 1 into a first chamber 6 confronting the first sealing member 3 and a second chamber 7 confronting the second sealing member 4. An engageable portion 2a is provided at a front end of the plunger rod 2 as shown in FIGS. 3 and 4 such that the plunger rod 2 is attached to the second sealing member 4 by the engageable portion 2a. Powdery medicament P is contained in the first compartment 6, while pharmaceutical liquid L is contained in the second compartment 7.

A front assembly 15 including an injection needle 10 and a cap 11 for covering the injection needle 10 so as to protect the injection needle 10 is mounted on an outer periphery of the front end portion of the tubular body 1. The cap 11 is made of synthetic resin. A finger grip 12 made of synthetic resin is mounted on an outer periphery of the rear end portion of the tubular body 1. The tubular body 1 is made of glass or synthetic resin and is formed, at its location corresponding to the first compartment 6, with a bypass 1a. The bypass 1a is formed by a bulge portion obtained by projecting radially outwardly a circumferential portion of a peripheral wall of the first compartment 6 of the tubular body 1. A marker line (temporary stop line) 1b indicative of a position where a front end of the intermediate sealing member 5 should be temporarily stopped in use is drawn forwardly of the bypass 1a of the tubular body 1.

As shown in FIGS. 3 and 4, the plunger rod 2 is made of synthetic resin and includes a rod body 2b having a circular sectional shape or a crossed sectional shape defined by ribs 8a and 8b. The engageable portion 2a and a circular or polygonal grip 2c are, respectively, provided at the front end and a rear end of the plunger rod 2. Meanwhile, a rod portion 2d is provided between the engageable portion 2a and the rod body 2b. A liquid absorbing material 16 for preventing leakage of the pharmaceutical liquid L from the second compartment 7 is fitted around the rod portion 2d.

As clearly shown in FIG. 4, a flexible retainer member or stopping structure 17 is formed integrally with the plunger rod 2 so as to project rearwards obliquely relative to an axis of the plunger rod 2 and radially outwardly from the plunger rod 2. In addition, a retainer portion or base portion 17a extending substantially perpendicularly to the axis of the plunger rod 2 is provided at a front of a base portion of the retainer member 17 and a boss 17b is provided on a distal end face of the retainer member 17. As will be described later, when the plunger rod 2 is depressed forwardly in use, the retainer portion 17a of the retainer member 17 is brought into contact with a rear end face 12a of the finger grip 12 so as to temporarily stop the plunger rod 2 such that the front end of the intermediate sealing member 5 is temporarily stopped at the marker line 1b. Namely, in the two-component type prefilled syringe K1, the retainer member 17 functions as a temporary stop means for temporarily stopping the plunger rod 2.

Meanwhile, a hollow or space 18 for receiving the retainer member 17 is formed on the plunger rod 2 so as to confront the retainer member 17 and a recess 18a for receiving the boss 17b when the retainer member 17 has been inserted into the hollow 18 is formed on the rib 8b of the plunger rod 2. The space 18 functions as a releasing structure that receives the stopping member 17. Furthermore, a notch 18b extending forwardly from the base portion of the retainer member 17 is provided in the hollow 18 so as to impart elasticity to the retainer member 17.

The intermediate sealing member 5 is constituted by front and rear intermediate sealing members 5a and 5b abutting each other. However, the intermediate sealing member 5 may also be formed by a single part without being formed by the two parts described above. The first sealing member 3, the second sealing member 4 and the intermediate sealing member 5 are formed by elastomer such as synthetic rubber.

Hereinafter, operation of the two-component type prefilled syringe K1 of the above described arrangement is described with reference to FIGS. 1A and 1B and FIGS. 2A and 2B. Initially, at the first operational position (storage position) of the two-component type prefilled syringe K1 shown in FIG. 1A, the plunger rod 2 is mounted on the second sealing member 4 by attaching the engageable portion 2a of the plunger rod 2 to the second sealing member 4. At this time, the retainer member 17 extends rearwards obliquely relative to the axis of the plunger rod 2 and radially outwardly from the plunger rod 2. Moreover, at this time, the powdery medicament P and the pharmaceutical liquid L are, respectively, contained in the first and second compartments 6 and 7 of the tubular body 1 and the front end of the intermediate sealing member 5 is disposed rearwards of the bypass 1a of the first compartment 6.

Figure 1A:
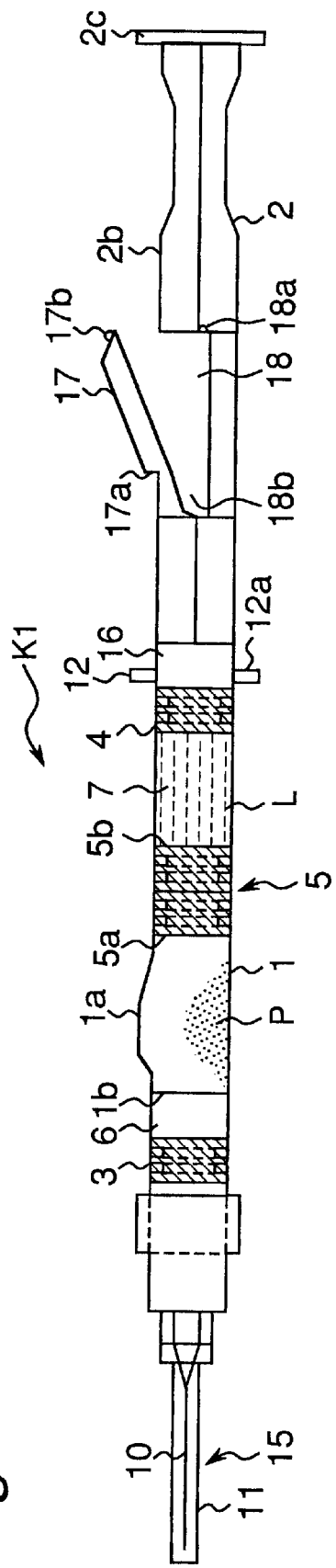
FIGS. 1A and 1B are schematic sectional views showing a first operational position (storage position) and a second operational position of a two-component type prefilled syringe according to a first embodiment of the present invention, respectively.
Figure 1B:
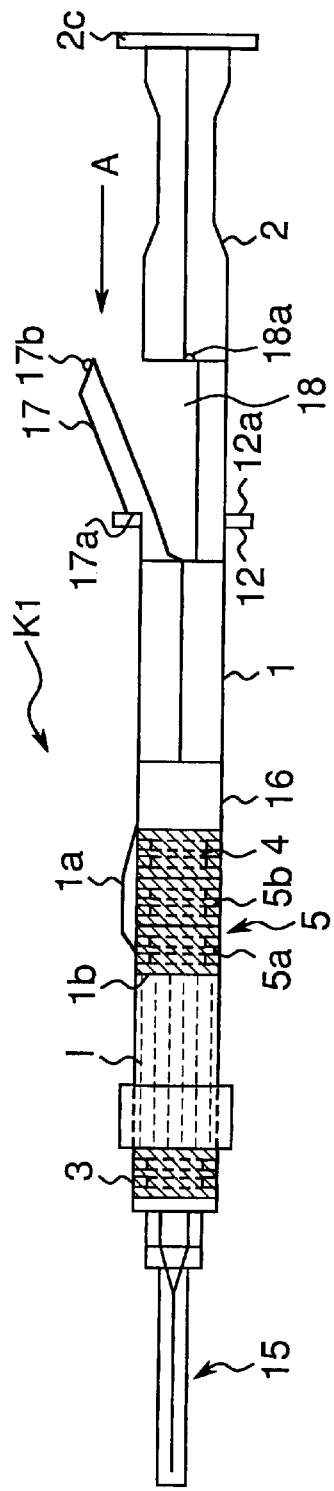

Then, at the second operational position of the two-component type prefilled syringe K1 shown in FIG. 1B, the retainer portion 17a of the retainer member 17 is brought into contact with the rear end face 12a of the finger grip 12 by depressing the plunger rod 2 in the direction of the arrow A, i.e. forwardly, so that the plunger rod 2 is stopped temporarily and thus, the front end of the intermediate sealing member 5 is temporarily stopped at the marker line 1b beyond the bypass 1a. At this time, the first sealing member 3 is stopped in the front assembly 15, while the second sealing member 4 is brought into contact with the intermediate sealing member 5. When the intermediate sealing member 5 is disposed in the bypass 1a during displacement of the front end of the intermediate sealing member 5 from the first operational position to the maker line 1b of the second operational position, the first and second compartments 6 and 7 are communicated with each other through the bypass 1a and thus, the pharmaceutical liquid L in the second compartment 7 is carried into the powdery medicament P in the first compartment 6 by the second sealing member 4. Subsequently, when the powdery medicament P is sufficiently dissolved or dispersed in the pharmaceutical liquid L by shaking the tubular body 1, injection liquid I is formed.

Subsequently, at the third operational position of the two-component type prefilled syringe K1 shown in FIG. 2A, the retainer member 17 is pushed in the direction of the arrow B, i.e. downwardly into the hollow 18 with a finger in a state where the plunger rod 2 is held at the second operational position, namely, the front end of the intermediate sealing member 5 is disposed at the marker line 1b. As a result, since the retainer member 17 and the finger grip 12 are brought out of contact with each other, it becomes possible to depress the plunger rod 2 further forwardly. At this time, since the boss 17b of the retainer member 17 is received by the recess 18a of the hollow 18a, the retainer member 17 is held in the hollow 18.

Thereafter, the cap 11 is removed from the two-component type prefilled syringe K1 and the plunger rod 2 is depressed slightly forwardly so as to discharge air from the injection needle 10 by filling the injection needle 10 to its distal end with the injection liquid I. Then, by depressing the plunger rod 2 forwardly until the intermediate sealing member 5 comes into contact with the first sealing member 3 together with the second sealing member 4, the injection liquid I is administered. As a result, the two-component type prefilled syringe K1 reaches the fourth operational position of FIG. 2B.

FIGS. 5A and 5B and FIGS. 6A and 6B show a first operational position (storage position), a second operational position, a third operational position and a fourth operational position of a two-component type prefilled syringe K2 according to a second embodiment of the present invention, respectively. In the two-component type prefilled syringe K2, the stopping structure for temporarily stopping the plunger rod 2 includes a frame member 20 which is retractably mounted on the plunger rod 2 so as to project radially outwardly from the plunger rod 2.

Figure 10B:
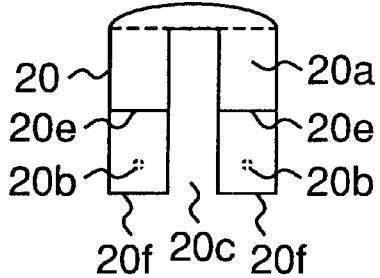
FIGS. 10A, 10B and 10C are an enlarged front elevational view, an enlarged left side elevational view and an enlarged bottom plan view of a frame member employed in the two-component type prefilled syringe of FIG. 5A, respectively.
Figure 10A:
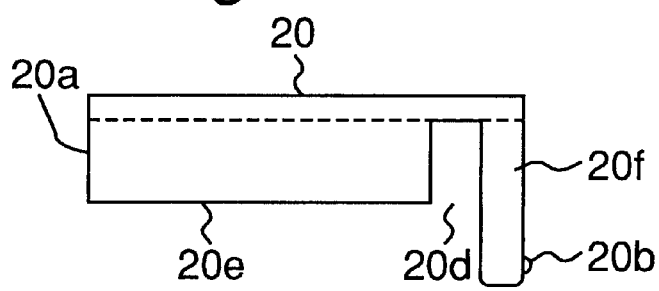
Figure 10C:
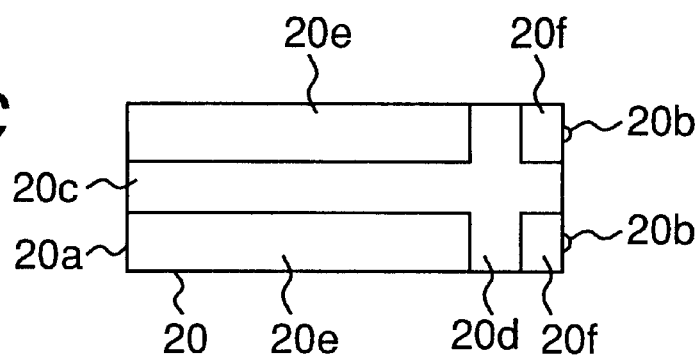

As shown in FIGS. 10A, 10B and 10C, the frame member 20 has a front end face 20a, a pair of protrusions 20b formed on a rear end face, a longitudinal slot 20c and a lateral slot 20d. A pair of leg portions 20e have the longitudinal slot 20c therebetween at a front side of the lateral slot 20d, while a pair of leg portions 20f extending further downwardly than the leg portions 20e have the longitudinal slot 20c therebetween at a rear side of the lateral slot 20d.

Figure 7:
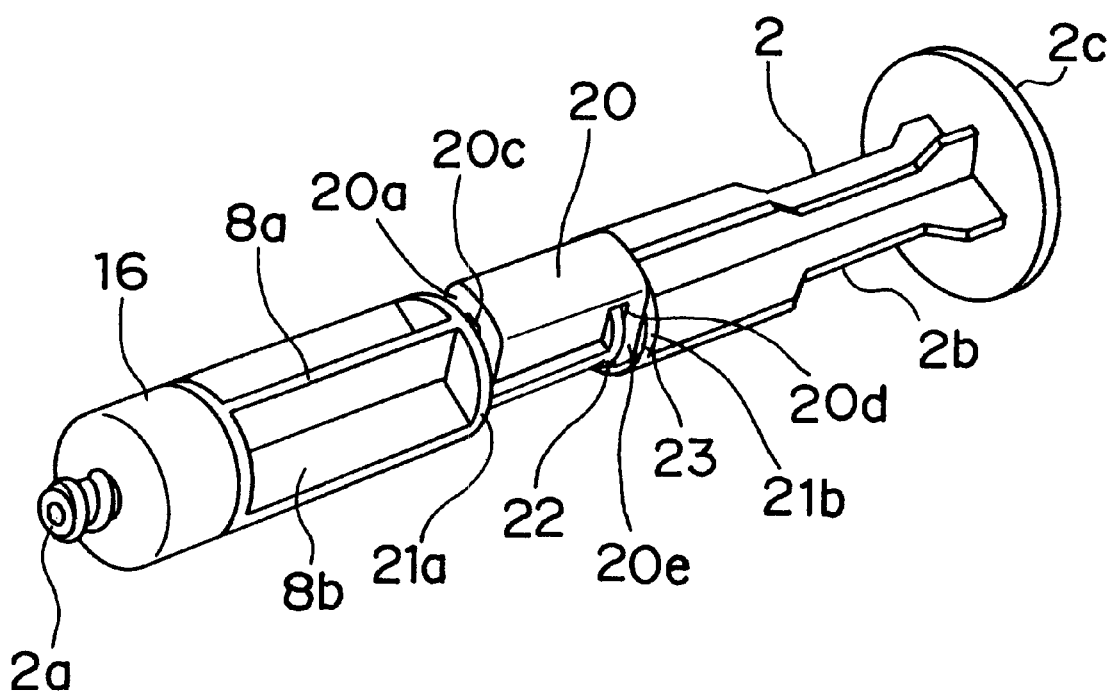
FIG. 7 is a perspective view of a plunger rod of the two-component type prefilled syringe of FIG. 5A.
Figure 8:
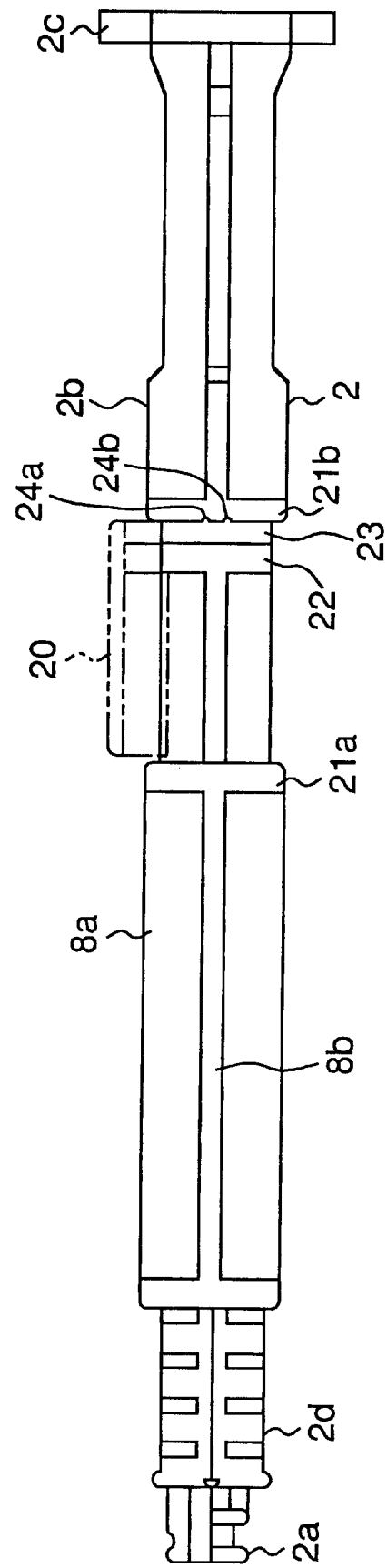
FIG. 8 is an enlarged front elevational view of the plunger rod of FIG. 7.
Figure 9:
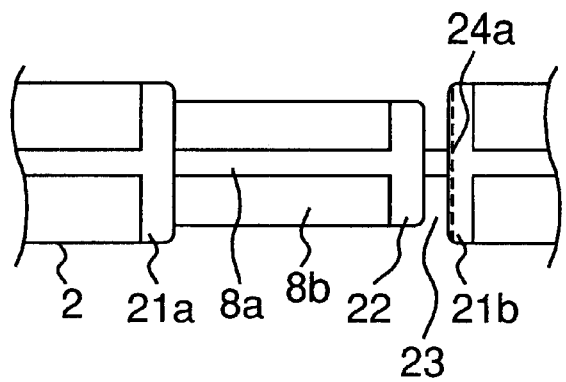
FIG. 9 is a fragmentary top plan view of the plunger rod of FIG. 7.

As shown in FIGS. 7 to 9, the plunger rod 2 includes a circular rib 22 disposed between a front circular rib 21a and a rear circular rib 21b and having a diameter smaller than that of the front and rear circular ribs 21a and 21b. An air gap 23 is defined between the circular rib 22 and the rear circular rib 21b. The air gap 23 functions as a releasing structure that receives the frame member 20. An upper slit 24a and a lower slit 24b are formed on the rear circular rib 21b so as to receive the protrusions 20b of the frame member 20 when the frame member 20 is projected radially outwardly from the plunger rod 2 and is received in the plunger rod 2, respectively. When the frame member 20 is mounted on the plunger rod 2, the protrusions 20b of the frame member 20 are received in the upper slit 24a of the rear circular rib 21b of the plunger rod 2 such that the frame member 20 is projected radially outwardly from the plunger rod 2. Furthermore, at this time, the rib 8a is inserted into the longitudinal slot 20c of the frame member 20 so as to be gripped by the leg portions 20e and 20f and the circular rib 22 is inserted into the lateral slot 20d so as to be gripped by the leg portions 20e and 20f Since the other construction of the two-component type prefilled syringe K2 is similar to the two-component type prefilled syringe K1, the description is abbreviated for the sake of brevity.

Hereinafter, operation of the two-component type prefilled syringe K2 of the above described arrangement is described with reference to FIGS. 5A and 5B and FIGS. 6A and 6B. Initially, at the first operational position (storage position) of the two-component type prefilled syringe K2 shown in FIG. 5A, the plunger rod 2 is mounted on the second sealing member 4 by attaching the engageable portion 2a of the plunger rod 2 to the second sealing member 4. At this time, since the protrusions 20b of the frame member 20 are received in the upper slit 24a of the plunger rod 2, the frame member 20 is projected radially outwardly from the plunger rod 2. In addition, at this time, the powdery medicament P and the pharmaceutical liquid L are, respectively, contained in the first and second compartments 6 and 7 of the tubular body 1 and the front end of the intermediate sealing member 5 is disposed rearwards of the bypass 1a of the first compartment 6.

Figure 5A:
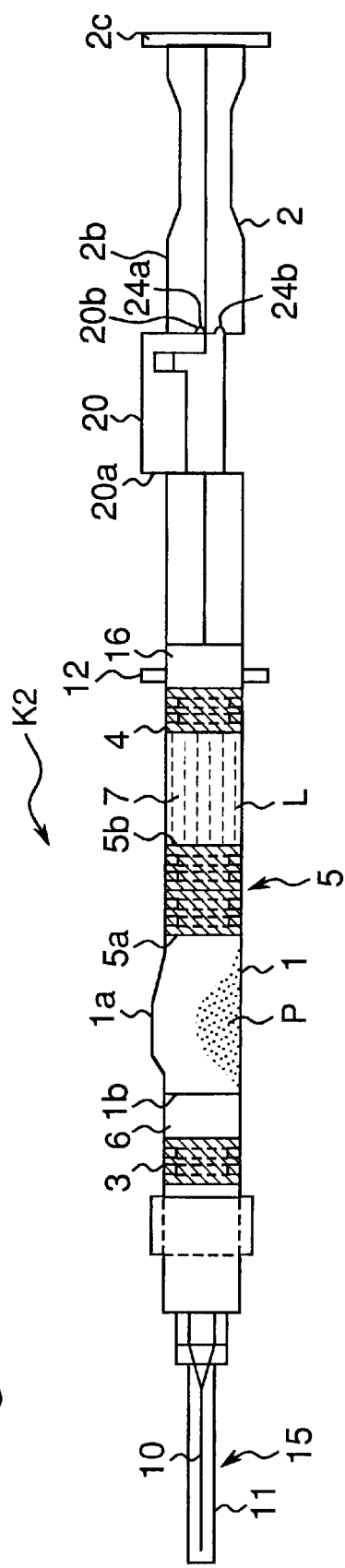
FIGS. 5A and 5B are schematic sectional views showing a first operational position (storage position) and a second operational position of a two-component type prefilled syringe according to a second embodiment of the present invention, respectively.
Figure 5B:
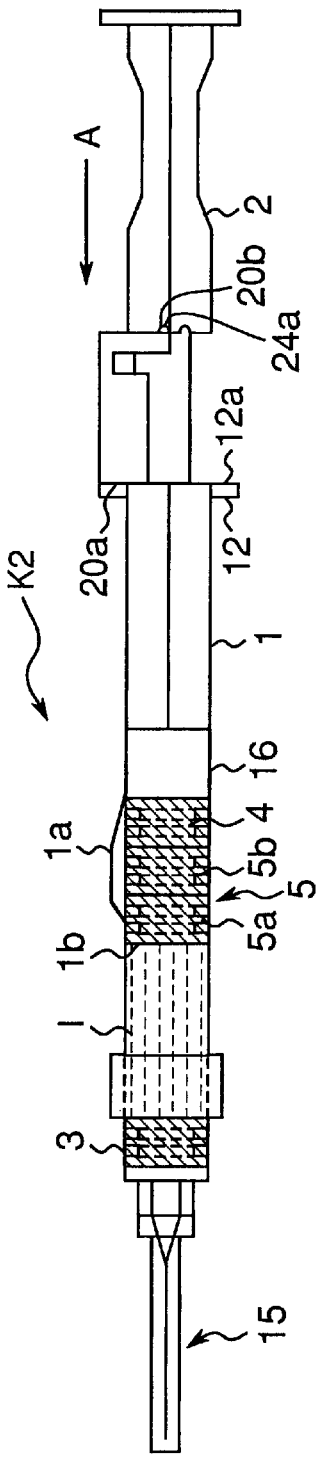

Then, at the second operational position of the two-component type prefilled syringe K2 shown in FIG. 5B, the front end face 20a of the frame member 20 is brought into contact with the rear end face 12a of the finger grip 12 by depressing the plunger rod 2 in the direction of the arrow A, i.e. forwardly, so that the plunger rod 2 is stopped temporarily and thus, the front end of the intermediate sealing member 5 is temporarily stopped at the marker line 1b beyond the bypass 1a. Thereafter, when the powdery medicament P is sufficiently dissolved or dispersed in the pharmaceutical liquid L by shaking the tubular body 1 in the same manner as the two-component type prefilled syringe K1, the injection liquid I is formed.

Figure 6A:
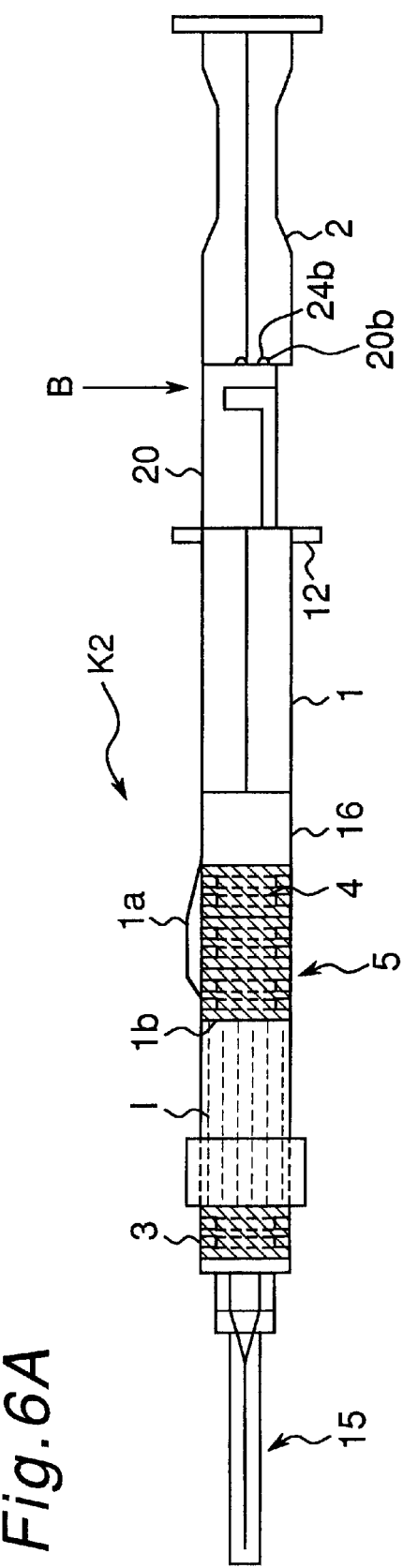
FIGS. 6A and 6B are schematic sectional views showing a third operational position and a fourth operational position of the two-component type prefilled syringe of FIG. 5A, respectively.
Figure 6B:
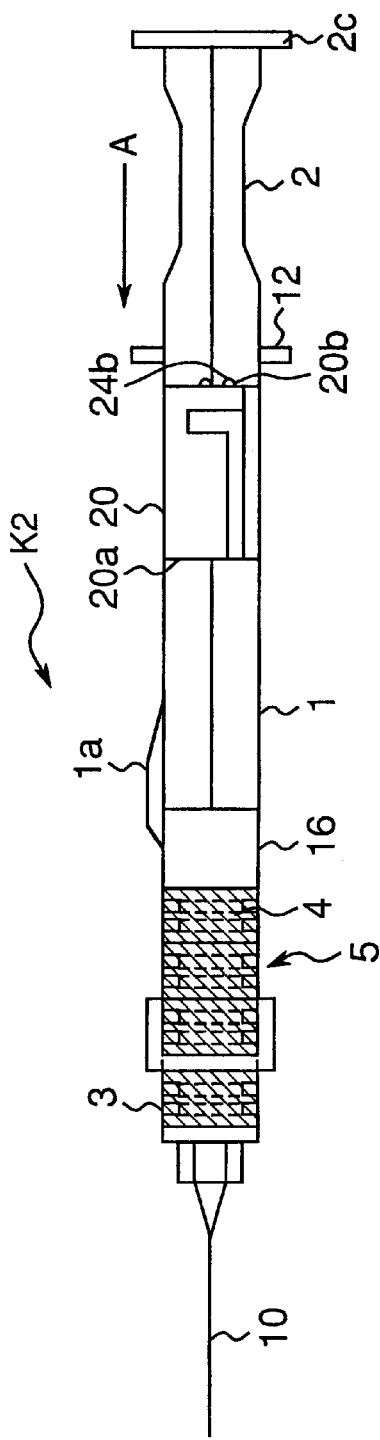

Subsequently, at the third operational position of the two-component type prefilled syringe K2 shown in FIG. 6A, the frame member 20 is pushed in the direction of the arrow B, i.e. downwardly into the air gap 23 of the plunger rod 2 with a finger to a state where the plunger rod 2 is held at the second operational position, namely, the front end of the intermediate sealing member 5 is disposed at the marker line 1b. At this time, the protrusions 20b of the frame member 20 are received in the lower slit 24b of the plunger rod 2. As a result, since the frame member 20 and the finger grip 12 are brought out of contact with each other, it becomes possible to depress the plunger rod 2 further forwardly.

Thereafter, the cap 11 is removed from the two-component type prefilled syringe K2 and the plunger rod 2 is depressed slightly forwardly so as to discharge air from the injection needle 10 by filling the injection needle 10 to its distal end with the injection liquid I. Then, by depressing the plunger rod 2 forwardly until the intermediate sealing member 5 comes into contact with the first sealing member 3 together with the second sealing member 4, the injection liquid I is administered. As a result, the two-component type prefilled syringe K2 reaches the fourth operational position of FIG. 6B.

Figure 13:
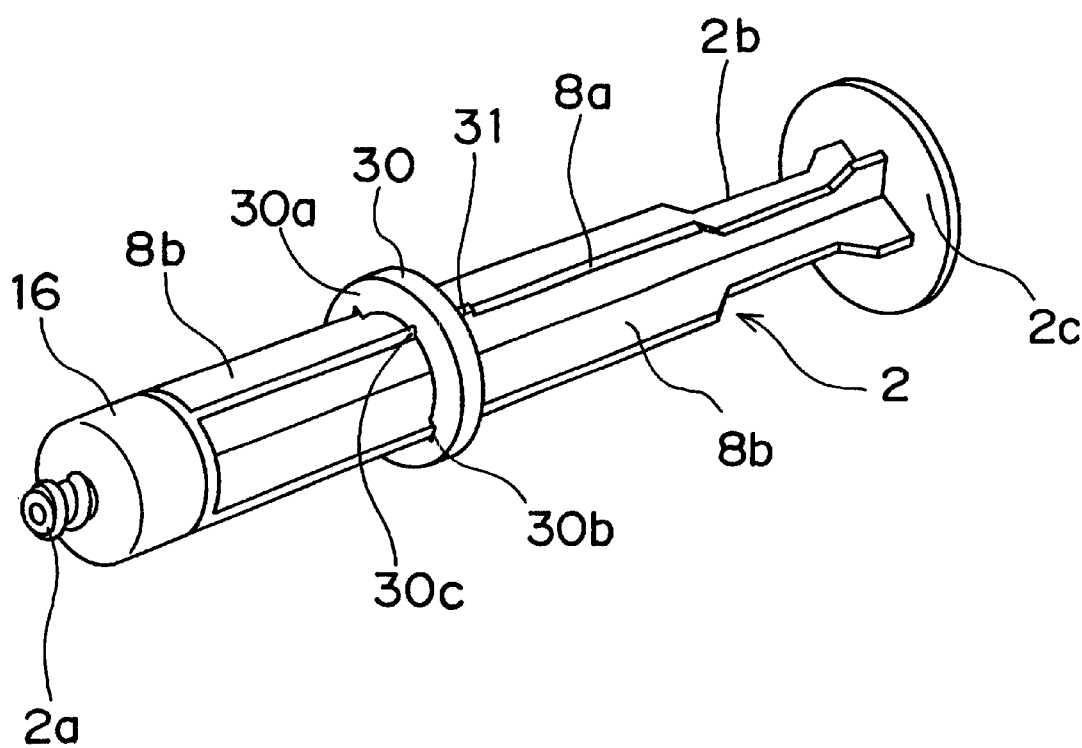
FIG. 13 is a perspective view of a plunger rod of the two-component type prefilled syringe of FIG. 11A.
Figure 14:
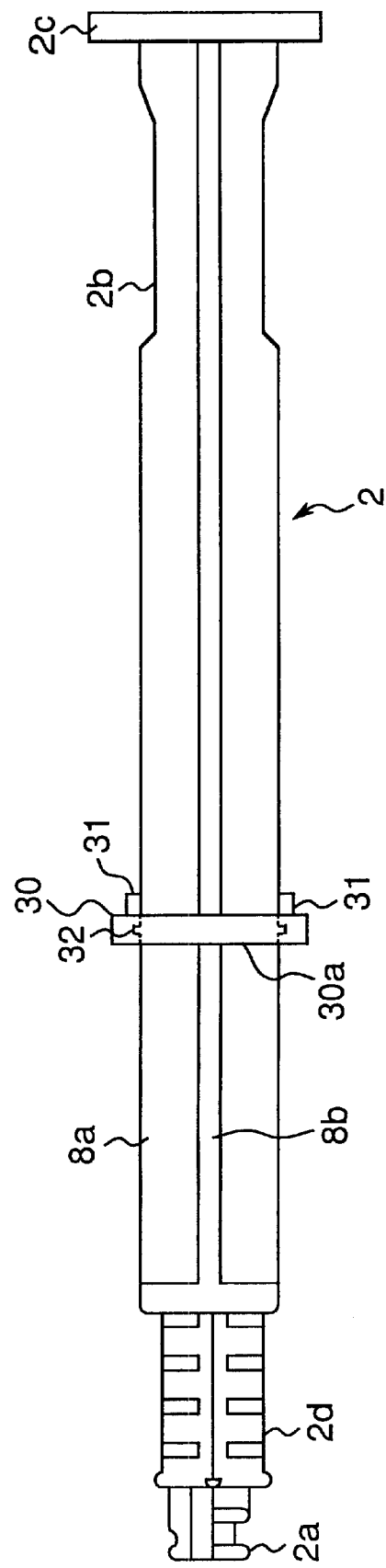
FIG. 14 is an enlarged front elevational view of the plunger rod of FIG. 13.
Figure 15:
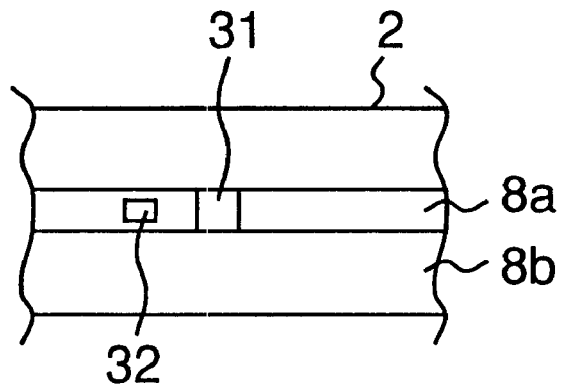
FIG. 15 is a fragmentary top plan view of the plunger rod of FIG. 14.

FIGS. 11A and 11B and FIGS. 12A and 12B show a first operational position (storage position), a second operational position, a third operational position and a fourth operational position of a two-component type prefilled syringe K3 according to the third embodiment of the present invention, respectively. In the two-component type prefilled syringe K3, the stopping structure for temporarily stopping the plunger rod 2 includes a pair of projections 31 provided on an outer periphery of the plunger rod 2 and a ring 30 which is rotatably fitted around the outer periphery of the plunger rod 2 so as to be retained in an axial direction of the plunger rod 2 by the projections 31. As shown in FIGS. 13 and 14, the projections 31 are, respectively, provided on upper and lower edges of the rib 8a and a pair of protuberances 32 smaller than the projections 31 are also provided on the upper and lower edges of the rib 8a so as to be spaced slightly away from the projections 31 in the axial direction of the plunger rod 2.

Figure 16:
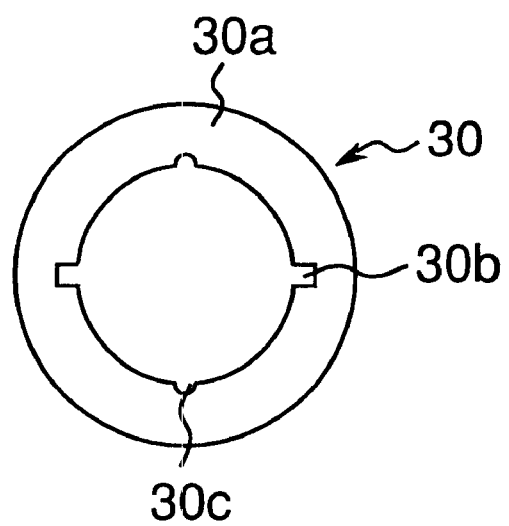
FIG. 16 is an enlarged front elevational view of a ring employed in the two-component type prefilled syringe of FIG. 11A.
Figure 17:
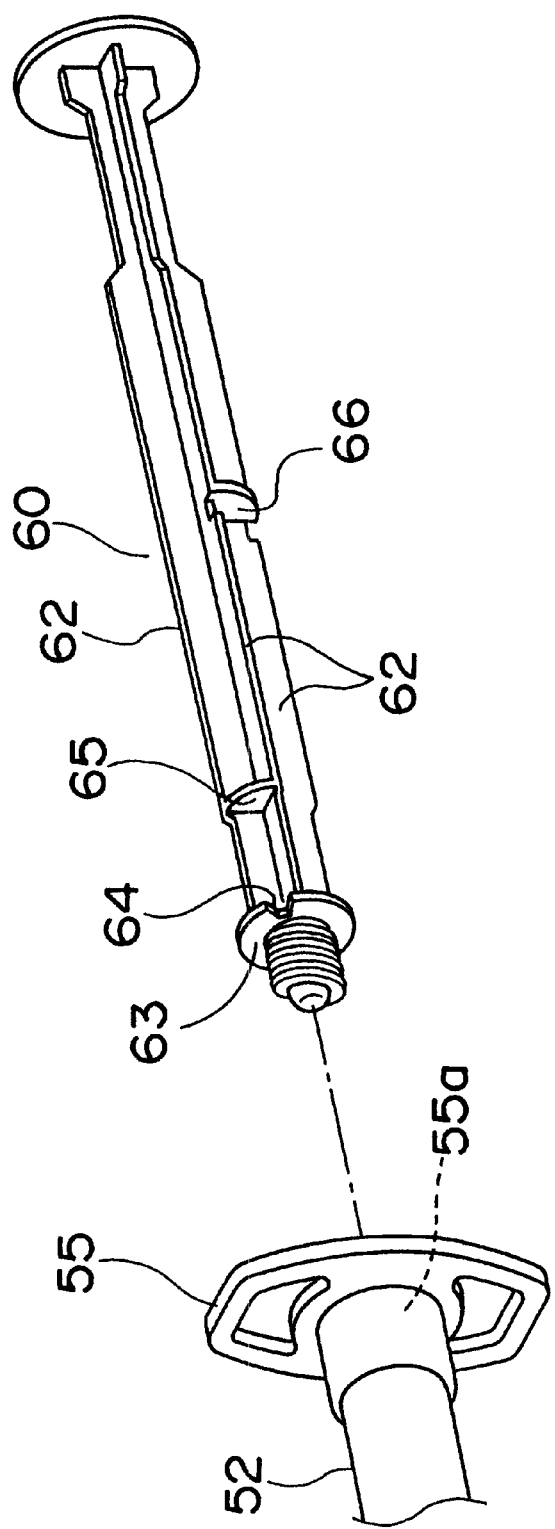
FIG. 17 is a fragmentary perspective view of a prior art prefilled syringe (already referred to)
Figure 18:
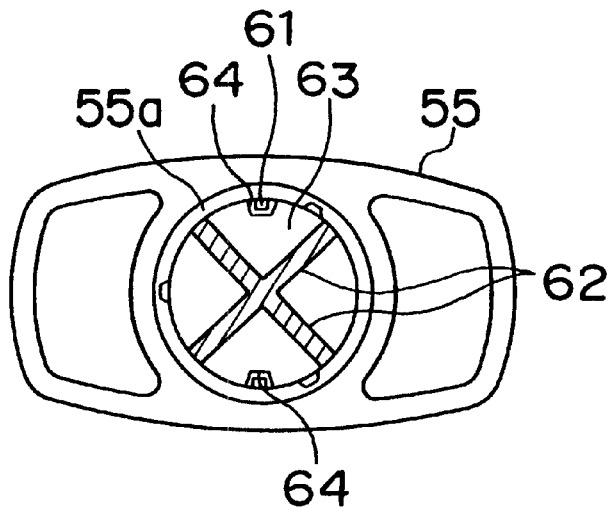
FIG. 18 is a partly sectional side elevational view of the prior art prefilled syringe of FIG. 17 (already referred to)
Figure 19:
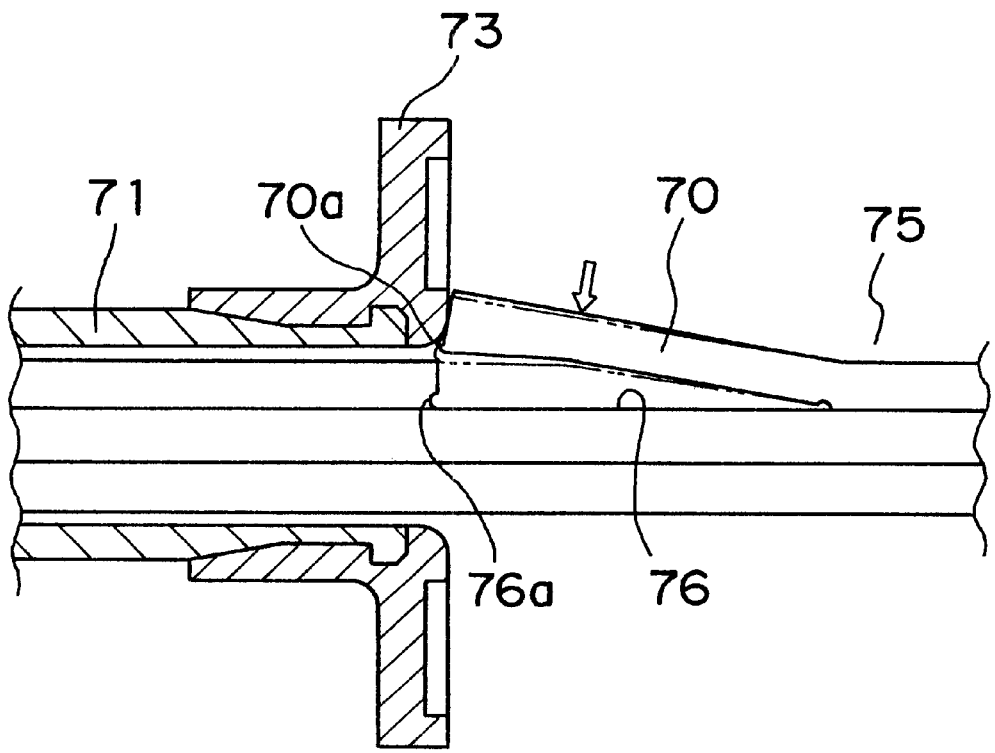
FIG. 19 is a partly sectional fragmentary front elevational view of another prior art prefilled syringe (already referred to).

Meanwhile, as shown in FIGS. 13, 14 and 16, the ring 30 has a front end face 30a and includes a pair of grooves 30b and a pair of recesses 30c. The grooves 30b are set at such dimensions as to allow the projections 31 to pass therethrough, whereby the grooves 30b function as releasing structure. On the other hand, the recesses 30c are set at such dimensions as to receive the protuberances 32 but prevent the projections 31 from passing therethrough. A straight line connecting the grooves 30b and a straight line connecting the recesses 30c intersect with each other orthogonally. When the ring 30 is fitted around the outer periphery of the plunger rod 2, the protuberances 32 of the plunger rod 2 are, respectively, received in the recesses 30c of the ring 30. Therefore, the ring 30 not only is retained in a circumferential direction of the plunger rod 2 by the protuberances 32 but is retained in the axial direction of the plunger rod 2 by the projections 31. However, the force of engagement between the protuberances 32 and the recesses 30c is small. Thus, when the ring 30 is rotated from this position through 90° with a force exceeding the force of engagement between the protuberances 32 and the recesses 30c, the recesses 30c cross over the protuberances 32 and the grooves 30b coincide in position with the projections 31. Therefore, since retention of the ring 30 in the axial direction of the plunger rod 2 by the projections 31 is cancelled, it becomes possible to depress the plunger rod 2 further forwardly. Since the other construction of the two-component type prefilled syringe K3 is similar to the two-component type prefilled syringe K1, the description is abbreviated for the sake of brevity.

Hereinafter, operation of the two-component type prefilled syringe K3 of the above described arrangement is described with reference to FIGS. 11A and 11B and FIGS. 12A and 12B. Initially, at the first operational position (storage position) of the two-component type prefilled syringe K3 shown in FIG. 11A, the plunger rod 2 is mounted on the second sealing member 4 by attaching the engageable portion 2a of the plunger rod 2 to the second sealing member 4. At this time, since the protuberances 32 of the plunger rod 2 are, respectively, received in the recesses 30c of the ring 30, the ring 30 not only is retained in the circumferential direction of the plunger rod 2 by the protuberances 32 but is retained in the axial direction of the plunger rod 2 by the projections 31. Furthermore, at this time, the powdery medicament P and the pharmaceutical liquid L are, respectively, contained in the first and second compartments 6 and 7 of the tubular body 1 and the front end of the intermediate sealing member 5 is disposed rearwards of the bypass 1a of the first compartment 6.

Figure 11A:
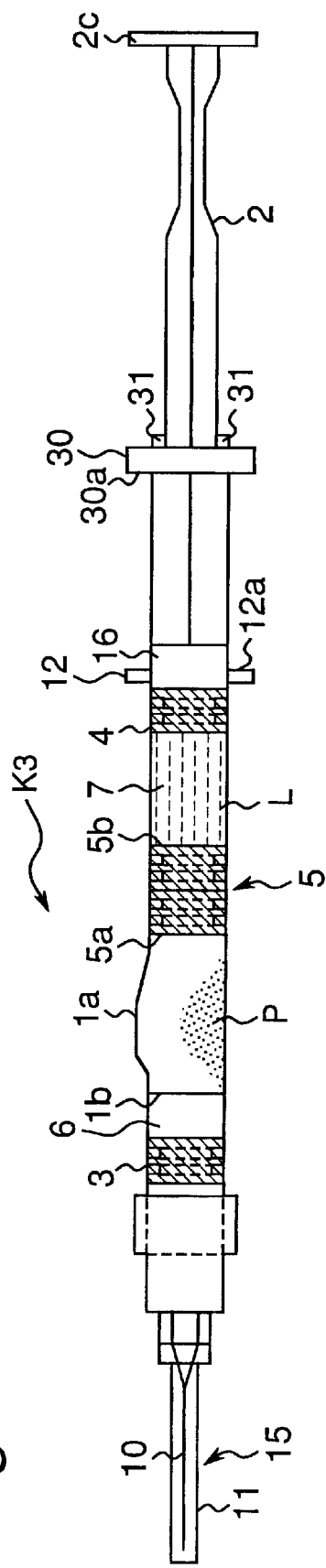
FIGS. 11A and 11B are schematic sectional views showing a first operational position (storage position) and a second operational position of a two-component type prefilled syringe according to a third embodiment of the present invention, respectively.
Figure 11B:
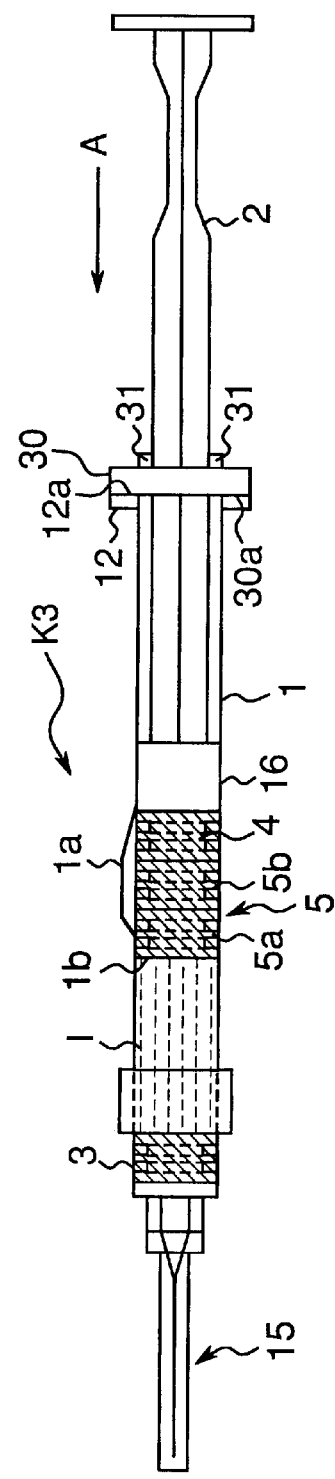

Then, at the second operational position of the two-component type prefilled syringe K3 shown in FIG. 11B, the front end face 30a of the ring 30 is brought into contact with the rear end face 12a of the finger grip 12 by depressing the plunger rod 2 in the direction of the arrow A, i.e. forwardly, so that the plunger rod 2 is stopped temporarily and thus, the front end of the intermediate sealing member 5 is temporarily stopped at the marker line 1b beyond the bypass 1a. Thereafter, when the powdery medicament P is sufficiently dissolved or dispersed in the pharmaceutical liquid L by shaking the tubular body 1 in the same manner as the two-component type prefilled syringe K1, the injection liquid I is formed.

Subsequently, at the third operational position of the two-component type prefilled syringe K3 shown in FIG. 12A, the ring 30 is rotated through 90° as shown by the arrow C in a state where the plunger rod 2 is held at the second operational position, namely, the front end of the intermediate sealing member 5 is disposed at the maker line 1b. As a result, since the grooves 30b coincide in position with the projections 31, retention of the ring 30 in the axial direction of the plunger rod 2 by the projections 31 is cancelled and thus, it becomes possible to depress the plunger rod 2 further forwardly.

Thereafter, the cap 11 is removed from the two-component type prefilled syringe K3 and the plunger rod 2 is depressed slightly forwardly so as to discharge air from the injection needle 10 by filling the injection needle 10 to its distal end with the injection liquid I. Then, by depressing the plunger rod 2 forwardly until the intermediate sealing member 5 comes into contact with the first sealing member 3 together with the second sealing member 4, the injection liquid I is administered. As a result, the two-component type prefilled syringe K3 reaches the fourth operational position of FIG. 12B.

The above described embodiments of the present invention are applied to the two-component type prefilled syringe. However, it is to be noted that the present invention is not restricted to the two-component type prefilled syringe but can also be applied to a one-component type prefilled syringe, a three-component type prefilled syringe, etc.

As is clear from the foregoing description of the prefilled syringe K1, since the retainer member 17 is elastically formed integrally with the plunger rod 2 so as to project rearwards obliquely relative to the axis of the plunger rod 2 and radially outwardly from the plunger rod 2, the retainer member 17 functions as the temporary stop means for temporarily stopping the plunger rod 2. Namely, when the plunger rod 2 is depressed forwardly in use, the retainer portion 17a provided at the front of the base portion of the retainer member 17 is brought into contact with the rear end face 12a of the finger grip 12 so as to temporarily stop the plunger rod 2 and thus, the front end of the intermediate sealing member 5 is temporarily stopped at the marker line 1b. By pushing the retainer member 17 downwardly into the hollow 18 with a finger in this state, the retainer member 17 and the finger grip 12 are brought out of contact with each other. Then, the injection liquid I is administered by depressing the plunger rod 2 further forwardly.

Therefore, in the prefilled syringe of the present invention, the temporary stop means constituted by the retainer member 17 not only is simple in structure and easy in operation but is capable of temporarily stopping the plunger rod 2 positively.

Furthermore, when the retainer member 17 is inserted into the hollow 18 in the prefilled syringe of the present invention, the plunger rod 2 is not required to be retracted and thus, there is no risk that air is sucked into the tubular body 1 from the injection needle 10.

What is claimed is:

1. An apparatus for use in administering a liquid, comprising:
   a tubular body having a front end portion with an open front end, and a rear end portion with an open rear end;
   a front end assembly mounted on an outer periphery of said front end portion of said tubular body;
   a finger grip mounted on an outer periphery of said rear end portion of said tubular body;
   a front sealing member within said front end portion of said tubular body;
   a rear sealing member within said tubular body; and
   a plunger rod that is axially movable within said tubular body such that said rear sealing member is axially moved within said tubular body upon axial movement of said plunger rod within said tubular body, with said plunger rod having
      (i) stopping structure that is to cooperate with said finger grip such that when said plunger rod and said rear sealing member are axially moved forwardly within said tubular body, said plunger rod is temporarily stopped from further forward axial movement via engagement of said stopping structure with said finger grip, whereby said rear sealing member is temporarily stopped at a predetermined position within said tubular body, with the predetermined position corresponding to a location at which administration of a liquid is to begin when said rear sealing member is axially moved forwardly therefrom, and
      (ii) releasing structure that is to cooperate with said stopping structure such that upon cooperation of said releasing structure with said stopping structure, the temporary stoppage of said plunger rod is released by disengaging said stopping structure from said finger grip without any one of
         (a) axially moving said plunger rod,
         (b) axially advancing said stopping structure relative to said plunger rod, and
         (c) removing said stopping structure from said plunger rod, whereby said plunger rod and said rear sealing member can then be further axially forwardly moved within said tubular member.

2. The apparatus according to claim 1, wherein
   said stopping structure comprises a flexible holding member that is integral with said plunger rod and projects obliquely rearwardly relative to an axis of said plunger rod and radially outwardly from said plunger rod, with said holding member having a base portion;
   said finger grip has a rear end face; and
   said releasing structure comprises a space within said plunger rod,
   such that said stopping structure is to cooperate with said finger grip to temporarily stop forward axial movement of said plunger rod by having said base portion of said holding member engage said rear end face of said finger grip, and such that said releasing structure is to cooperate with said stopping structure to release the temporary stoppage of said plunger rod by having said holding member be received within said space upon flexing of said holding member relative to said plunger rod in a direction that is rearward and toward the axis of said plunger rod, whereby said base portion of said holding member becomes disengaged from said rear end face of said finger grip.

3. The apparatus according to claim 2, wherein said base portion of said holding member extends substantially perpendicularly to the axis of said plunger rod.

4. The apparatus according to claim 1, wherein
   said stopping structure comprises a frame member that is retractably mounted on said plunger rod so as to project radially outwardly from said plunger rod when not in a retracted position, with said frame member having a front end face;

said finger grip has a rear end face; and said releasing structure comprises an air gap in said plunger rod, such that said stopping structure is to cooperate with said finger grip to temporarily stop forward axial movement of said plunger rod by having said front end face of said frame member engage said rear end face of said finger grip when said frame member is not in the retracted position, and such that said releasing structure is to cooperate with said stopping structure to release the temporary stoppage of said plunger rod by having said frame member be received within said air gap upon radial retraction of said frame member, whereby said front end face of said frame member becomes disengaged from said rear end face of said finger grip.

5. The apparatus according to claim 1, wherein said stopping structure comprises a projection on an outer periphery of said plunger rod and a ring that is rotatably fitted around the outer periphery of said plunger rod, with said ring having a front end face;

said finger grip has a rear end face; and said releasing structure comprises a groove formed on an inner periphery of said ring, with said groove being of dimensions that allow said projection to pass through said groove, such that said stopping structure is to cooperate with said finger grip to temporarily stop forward axial movement of said plunger rod by having said front end face of said ring engage said rear end face of said finger grip when said projection and said groove are not aligned, and such that said releasing structure is to cooperate with said stopping structure to release the temporary stoppage of said plunger rod by having said projection become aligned with said groove upon rotation of said ring.

* * * * *